(12) United States Patent
Boll et al.

(10) Patent No.: US 6,927,402 B2
(45) Date of Patent: Aug. 9, 2005

(54) DEVICE FOR DETECTING DIFFERENT FLUORESCENCE SIGNALS OF A SAMPLE SUPPORT ILLUMINATED WITH DIFFERENT EXCITATION WAVELENGTHS

(75) Inventors: Peter Boll, Weilheim (DE); Franz Drobner, München (DE); Christian Kassel, Putzbrunn (DE)

(73) Assignee: Siemens Aktiengesellschaft, Munich (DE)

( * ) Notice: Subject to any disclaimer, the term of this patent is extended or adjusted under 35 U.S.C. 154(b) by 172 days.

(21) Appl. No.: 10/343,795
(22) PCT Filed: Aug. 3, 2001
(86) PCT No.: PCT/DE01/02982
§ 371 (c)(1),
(2), (4) Date: Feb. 4, 2003
(87) PCT Pub. No.: WO02/12862
PCT Pub. Date: Feb. 14, 2002

(65) Prior Publication Data
US 2003/0168610 A1 Sep. 11, 2003

(30) Foreign Application Priority Data
Aug. 4, 2000 (DE) .......................................... 100 38 185

(51) Int. Cl.⁷ .............................................. G01N 21/64
(52) U.S. Cl. .................................. 250/458.1; 250/459.1
(58) Field of Search .......................... 250/458.1, 459.1, 250/461.1, 461.2; 356/73, 317, 417

(56) References Cited

U.S. PATENT DOCUMENTS

| 5,053,626 A | | 10/1991 | Tillotson | |
| 5,149,972 A | * | 9/1992 | Fay et al. | 250/461.1 |
| 5,491,343 A | | 2/1996 | Brooker | |
| 5,535,293 A | | 7/1996 | Buchin | |
| 5,760,900 A | * | 6/1998 | Ito et al. | 356/338 |
| 6,020,591 A | * | 2/2000 | Harter et al. | 250/458.1 |
| 6,628,385 B1 | * | 9/2003 | Osipchuk et al. | 356/318 |
| 2002/0055179 A1 | * | 5/2002 | Busey et al. | 436/172 |
| 2003/0161039 A1 | * | 8/2003 | Fukano et al. | 359/388 |
| 2003/0191368 A1 | * | 10/2003 | Wang et al. | 600/160 |

FOREIGN PATENT DOCUMENTS

| DE | 1291533 | 3/1969 |
| DE | 2147142 | 6/1974 |
| DE | 3915421 | 11/1990 |
| DE | 3926090 | 7/1991 |
| DE | 19748211 | 5/1999 |
| GB | 1599349 | 9/1981 |

* cited by examiner

Primary Examiner—Otilia Gabor
(74) Attorney, Agent, or Firm—Harness, Dickey & Pierce P.L.C.

(57) ABSTRACT

Light sources are provided for generating rays of light of different excitation wavelengths, which can be directed toward the sample support by excitation optics. The fluorescent light emitted each time by the sample support can be directed toward a receiver, which generates corresponding fluorescence signals. A mirror assembly with reflective areas and transparent areas is connected between the different light sources and the sample support. The mirror assembly can be displaced in such a manner that the ray of light of a light source passes through a transparent area and reaches the sample support.

18 Claims, 2 Drawing Sheets

DEVICE FOR DETECTING DIFFERENT FLUORESCENCE SIGNALS OF A SAMPLE SUPPORT ILLUMINATED WITH DIFFERENT EXCITATION WAVELENGTHS

This application is the national phase under 35 U.S.C. § 371 of PCT International Application No. PCT/DE01/02982 which has an International filing date of Aug. 3, 2001, which designated the United States of America and which claims priority on German Patent Application number DE 100 38 185.5 filed Aug. 4, 2000, the entire contents of which are hereby incorporated herein by reference.

FIELD OF THE INVENTION

The present invention generally relates to a device for detecting different fluorescence signals of a sample carrier illuminated by different excitation wavelengths.

BACKGROUND OF THE INVENTION

Wherever quantitative fluorescence immunoassays; for example, are carried out, sample carriers are known that have a multiplicity of electrodes, for example 10,000 electrodes, to which an electric voltage can be applied selectively. If different sample liquids are led over the electrodes, different samples can be produced by deposition at the electrodes, depending on the application of specific voltages. Since these samples are marked by two or more fluorescence carriers, they luminesce differently in the case of excitation by different optical wavelengths. Biochemical properties can be measured in this way.

It is known in this connection to use dichroic, permanently installed mirrors in order to achieve a separation of the different fluorescence wavelengths that are emitted by the sample carrier. In this case, a problem exists in that dichroic mirrors can be operated typically only when the beam path is parallel to the position of the dichroic mirrors. In addition, such mirrors are not 100% efficient. At the same time, they also require the excitation sources to be electrically clocked.

Sample carriers produced using semiconductor technology are, for example, built up in several layers and have a multiplicity of cylindrical platinum electrodes to which it is possible to apply the abovementioned voltages. The sample carriers are arranged in plastic containers covered in each case with a glass layer, it being possible for the sample liquids to flow through the space between the glass layer and plastic container and come into contact in the process with electrodes.

Document DE 39 26 090 C2 discloses a dual-beam photometer in which a rotatable mirror system divided into silvered and transmitting sectors is used to split a light bundle issuing from a light source into a measuring beam and into a reference beam. The two beam paths are recombined by the same mirror system, the measuring beam penetrating the mirror system and passing through a sample to be examined, and the reference beam being reflected at the mirror system and therefore not impinging on the sample. The recombined beam is detected by a detector device. Consequently, the influence of fluctuations in the light source brightness or the detector sensitivity can be eliminated given suitable evaluation of the detected measuring signals. DE 39 26 090 C2 further discloses in accordance with an exemplary embodiment a dual-beam photometer having a second light source emitting a continuous spectrum (see FIG. 4), whose radiation is used in a fashion alternating with the first light source both as measuring beam and as a reference beam when a mirror system divided into four sectors (two silvered and two transparent sectors) is used. It is possible in this way additionally to achieve compensation of background radiation.

SUMMARY OF THE INVENTION

An embodiment of the present invention includes creating a device for detecting different fluorescence signals of a sample carrier illuminated by different excitation waves, in the case of which it may not be necessary to clock the light sources generating the different excitation wavelengths.

In order to detect fluorescence signals of a sample carrier illuminated by different, preferably two, excitation wavelengths, dichroic mirrors are not used. In the case of an embodiment according to the present invention, a separation of the fluorescence signals is performed with the aid of a rotatable mirror arrangement that is arranged in the beam path of the excitation and detection optical system and is partly transmitting in accordance with the number of the excitation wavelengths. This mirror arrangement is moved in the beam path such that in each case one excitation detection channel is opened and the other excitation detection channels are closed. The mirror arrangement to may be a rotatable mirror.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
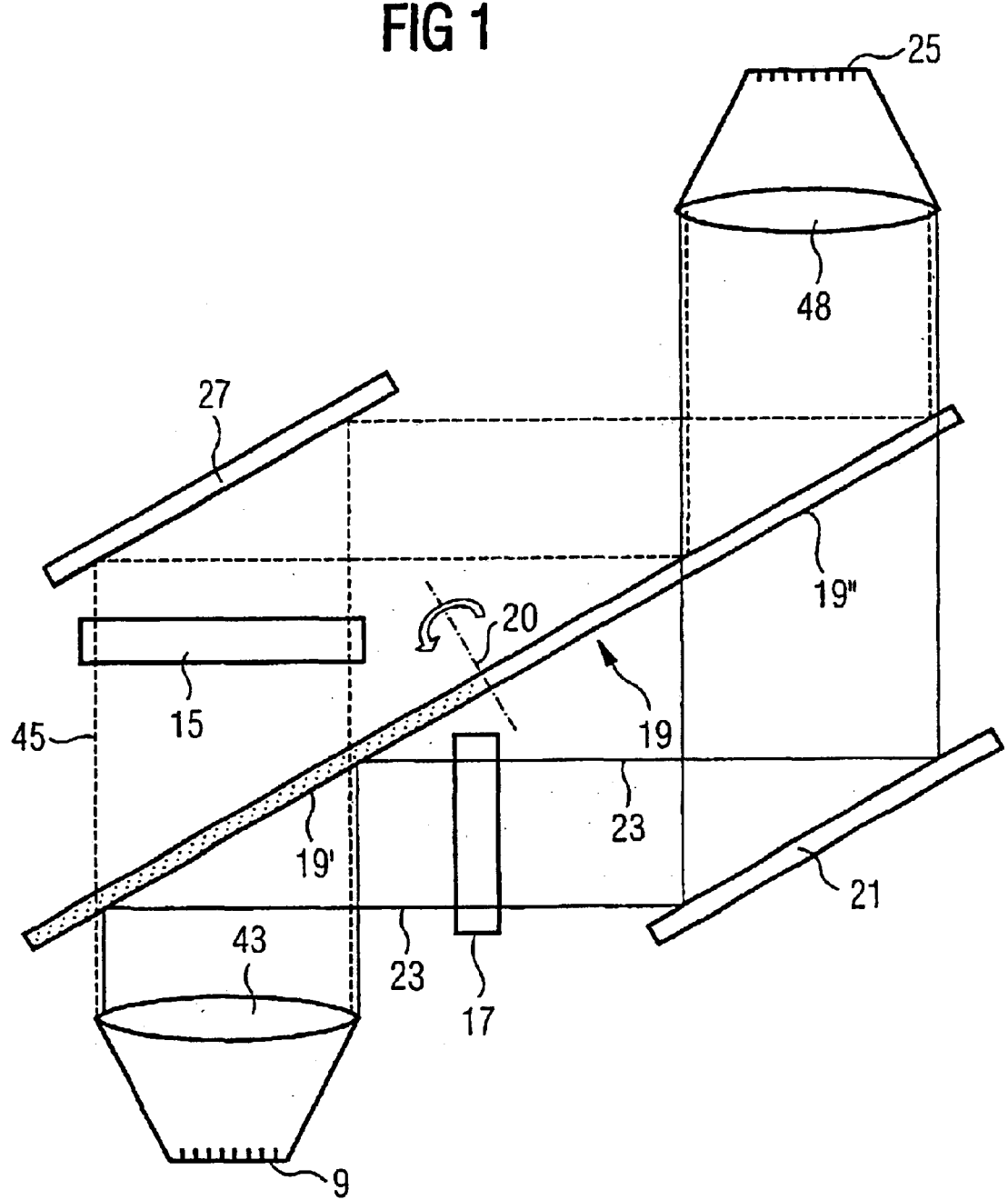
FIG. 1 illustrates a schematic of a first side view of a detection part of a device according to an embodiment of the present invention for detecting two different fluorescence signals of a sample carrier illuminated by two different excitation waves.
Figure 2:
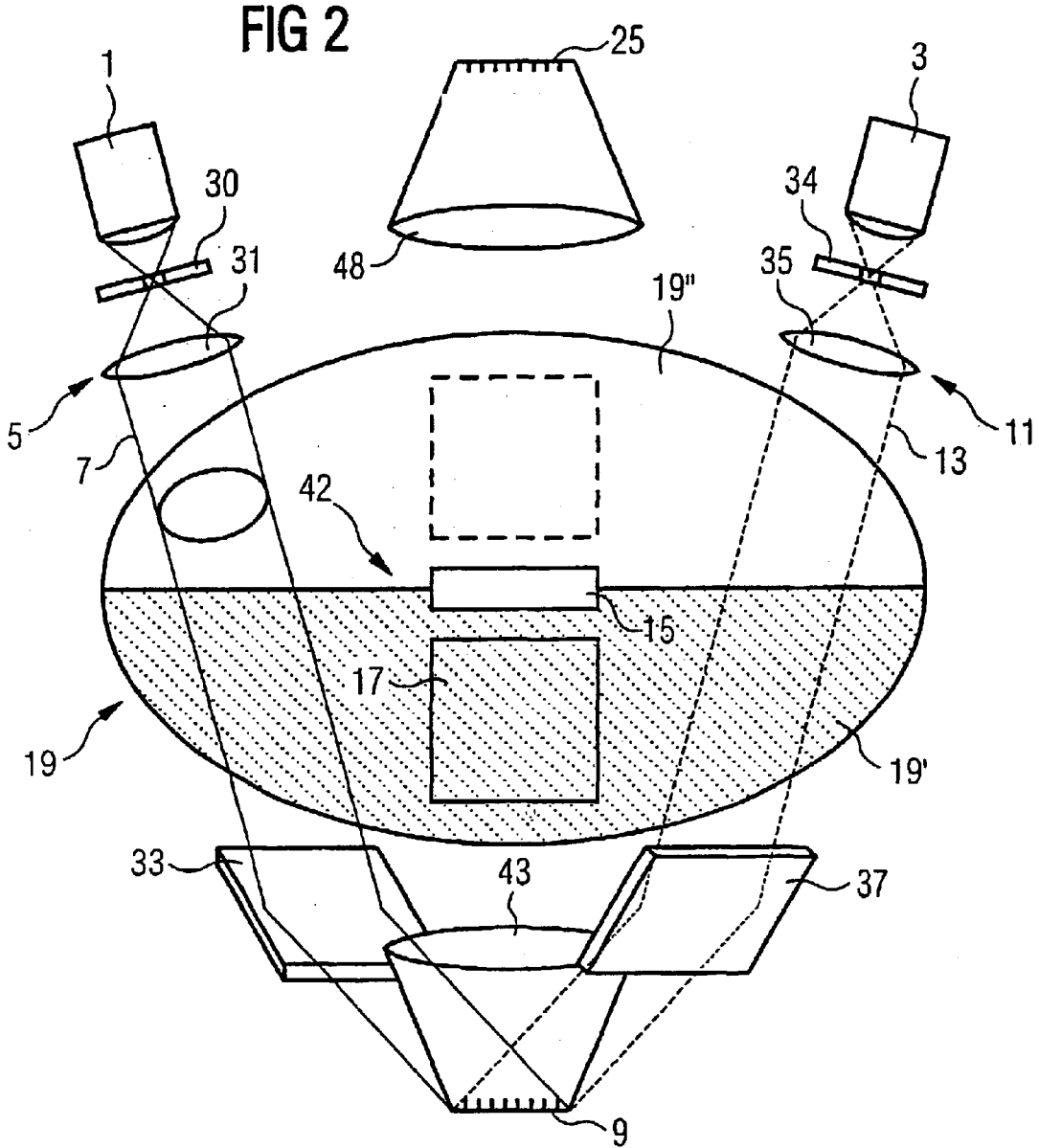
FIG. 2 illustrates a side view of the entire device of FIG. 1 at a viewing angle rotated by 90°.
Figure 3:
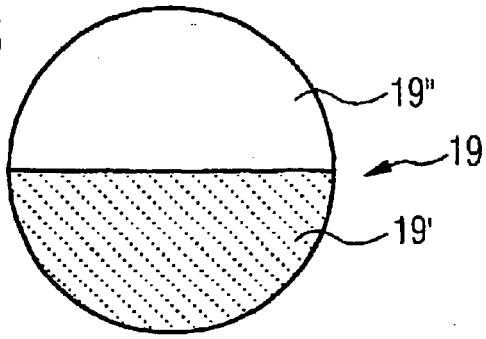
FIG. 3 illustrates a plan view of a rotatable mirror that is suitable for a device for detecting two different fluorescence signals in the case of two different excitation waves.

In accordance with FIGS. 1 to 3, an embodiment of the present invention, for detecting two different fluorescence signals in the case of two excitation wavelengths, essentially has a first light source 1, a second light source 3, and a first excitation optical system 5 that directs the first light beam 7 from the first light source 1 onto a sample carrier 9. Moreover, the embodiment includes a second excitation optical system 11 that directs the second light beam 13 from the second light source 3 onto the sample carrier 9, a first filter 15 assigned to a first fluorescent light, a second filter 17 assigned to a second fluorescent light, as mirror arrangement a segmented rotatable mirror 19 that in accordance with FIG. 3 has a first transmitting region 19" and a second reflecting region 19', a first fixed mirror 21 that reflects the first fluorescent light 23 to the receiver 25, and a second fixed mirror 27 that leads the second fluorescent light to the rotatable mirror 19 from which it is reflected to the receiver 25.

The first light source 1 and the second light source 3 may be laser sources, the first light source 1 generating, for example, a laser light of wavelength 532 nm, and the second light source 3 generating, for example, a laser light of wavelength 632 nm. The filters 15 and 17 are preferable steep-edge filters that either allow only the first or the second fluorescent light to pass. The first excitation optical system 5 comprises a first stop 30 and a first lens arrangement 31 that generate from the first laser beam generated by the first light source 1 a first parallel beam 7, and a first deflecting mirror 33 that directs the parallel beam 7 onto the sample carrier 9 in such a way that the latter is illuminated over its entire surface.

Correspondingly, the second excitation optical system 11 includes a second stop 34 and a second lens arrangement 35 that generate a second parallel beam 13 from the second laser beam from the second light source 3, and a second fixed deflecting mirror 37 that directs the parallel beam 13 onto the sample carrier 9 in order to illuminate the entire surface of the latter.

The rotatable mirror 19 can be rotated about an axis 20 of rotation and has the reflecting region 19' and the transmitting region 19" that, in the case of the use of two light sources 1, 3 of two different wavelengths, preferably correspond in each case to half the surface of the circular rotatable mirror 19.

The detection optical system 42 includes an optical imaging arrangement 43 that is arranged downstream of the sample carrier 9 and generates a parallel beam in each case from the first and second fluorescent light 23 and 45, respectively, output by the sample carrier 9, and an optical imaging arrangement 48 that is arranged upstream of the receiver 25 and projects the said parallel beams onto the entire surface of the receiver 25. The filter 15 and the fixed mirror 27 as well as the filter 17 and the fixed mirror 21 are part of the detection optical system 42.

The receiver 25 may be a CCD arrangement that, in accordance with the number of samples of the sample carrier 9, has photosensitive elements that respectively generate a first or second electric fluorescence signal in accordance with their illumination by the first or second fluorescent light 23 and 45, respectively. These fluorescence signals are led to an electronic evaluation system (not illustrated in more detail).

For example, the sample carrier 9 and the receiver 25 have samples or optical sensor elements in mutually corresponding raster configurations, the number of samples or sensor elements being of the order of 10 000.

The function of an embodiment of the present invention for separating two fluorescence signals is explained below in more detail.

It is assumed in this case that the reflecting region 19' is located in a phase in FIG. 1 to the left of the axis 20 of rotation, and the transmitting region 19" is located to the right of the axis 20 of rotation. The result of this is that the first laser beam 7 generated by the first light source 1 passes through the transmitting region 19" and is led to the sample carrier 9 by the imaging optical system 5 (FIG. 2) in order to illuminate the entire surface of the latter. The first fluorescent light 23 emitted by the sample carrier 9 as a consequence of the wavelength of the first laser beam 7 is reflected at the reflecting region 19' and directed onto the filter 17, passes through the latter, is reflected at the fixed mirror 21, passes through the transmitting region 19" of the mirror 19 (FIG. 1) and is directed by the imaging optical system 48 onto the receiver 25, which generates corresponding fluorescence signals at its individual photosensitive sensor elements. During this phase, the laser beam 13 emitted by the second light source 3 is reflected at the reflecting region 19' such that it cannot reach the second deflecting mirror 37 and cannot reach the sample carrier 9 (FIG. 2).

In the other phase, in which the reflecting region 19' is located to the right of the axis 20 of rotation, and the transmitting region 19" is located to the left of the axis 20 of rotation, the second laser beam 13 from the light source 3 passes through the transmitting region 19" and is directed by the second deflecting mirror 37 onto the sample carrier 9 (FIG. 2 with interchanged regions 19', 19"). The second fluorescent light 45 generated in this case passes through the transmitting region 19", passes the filter 15, is reflected by the fixed mirror 27 to the reflecting region 19' of the rotatable mirror 19 and is reflected at the latter and directed to the imaging optical system 44 (FIG. 1, dotted lines). The latter projects the second fluorescent light 45 onto the receiver 25. The individual optical sensor elements of the receiver 25 then generate corresponding second fluorescence signals. In this phase, the first laser beam generated by the first light source 1 is reflected at the reflecting region 19' such that it cannot reach the first deflecting mirror 33 and also cannot reach the sample carrier 9.

It is possible in this way to use the rotary movement of the rotatable mirror 19 to switch back and forth between the two laser beams 7 and 13, which are generated simultaneously, in order respectively to be able to illuminate the entire surface of the sample carrier 9, such that in each case only one laser beam illuminates the sample carrier 9 and a fluorescent light is generated that is led to the receiver 25, while the respective other laser beam is reflect at the reflecting region 19" of the rotatable mirror 19 such that it cannot reach the receiver 25. Consequently, the different fluorescence signals are received in successive sequence at the receiver 25 and, if the receiver 25 is a CCD arrangement, are latched to an electronic evaluation device.

It may be pointed out that in order to separate more than two fluorescence signals it is also possible for the rotatable mirror 19 to have a plurality of transparent and reflecting regions so as to ensure that in different phases it is always only one fluorescent light that is excited by a laser beam and led to the receiver, while the respective other laser beams are reflected at the reflecting regions such that they cannot excite fluorescent light.

It is also possible to use other movable mirror arrangement instead of the rotatable mirror 19 explained. For example, a transparent and reflecting regions can be moved back and forth next to one another in a plate having row, this being done in the direction of the row.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for detecting different fluorescence signals of a sample carrier illuminated over a surface thereof by different excitation wavelengths, the excitation wavelengths having a plurality of samples excited by different optical wavelengths to output different fluorescent light, comprising:

a first light source and a second light source being provided for generating light beams of different optical wavelengths, the light beams being directed via an excitation optical system toward a surface of a sample carrier;

fluorescent light emitted by the sample carrier being directed to a receiver, wherein said receiver generates fluorescence signals based on the fluorescent light being projected onto a photosensitive element of the receiver; and a mirror arrangement with silvered and transmitting regions being connected between the light sources and the sample carrier; wherein in a first operating state, a first light beam of the first light source passes through a transmitting region to the sample carrier, and a second light beam from the second light source is reflected from the silvered region such that it does not reach the sample carrier, and a first fluorescent light is emitted from the sample carrier to the reflecting region, which reflects it to a first fixed mirror, and that the first fixed mirror reflects the first fluorescent light through the transmitting region to the receiver, the receiver being screened from the light sources in such a way that the receiver detects fluorescent light emitted by the plurality of samples, and in a second operating state, the second light beam of the second light source passes through the transmitting region to the sample carrier, and the first light beam from the first light source is reflected from the silvered region such that it does not reach the sample carrier, and a second fluorescent light is emitted from the sample carrier to the reflecting region, which reflects it to a second fixed mirror, and the second fixed mirror reflects the second fluorescent light through the transmitting region to the receiver, the receiver being screened from the light sources in such way that the receiver detects fluorescent light emitted by the plurality of samples.

2. The device as claimed in claim 1, wherein the mirror arrangement is a mirror that is rotatable about an axis.

3. The device as claimed in claim 2, wherein the rotatable mirror is of circular design and has a semicircular transmitting region and a semicircular reflecting region.

4. The device as claimed in claim 2, wherein the first light beam is directable via a first excitation optical system to the sample carrier in order to illuminate the entire surface of the latter.

5. The device as claimed in claim 2, wherein the second light beam is directable by a second excitation optical system to the sample carrier in order to illuminate the entire surface of the latter.

6. The device as claimed in claim 2, wherein a first filter is provided between the sample carrier and the receiver in the beam path of the first fluorescent light, the first filter passing only the first fluorescent light.

7. The device as claimed in claim 1, wherein the excitation optical system includes the first light beam being directable via a first excitation optical system to the sample carrier in order to illuminate the entire surface of the latter.

8. The device as claimed in claim 7, wherein the first excitation optical system has a first deflecting mirror that directs the first light beam to the sample carrier.

9. The device as claimed in claim 7, wherein the second light beam is directable by a second excitation optical system to the sample carrier in order to illuminate the entire surface of the latter.

10. The device as claimed in claim 7, wherein a first filter is provided between the sample carrier and the receiver in the beam path of the first fluorescent light, the first filter passing only the first fluorescent light.

11. The device as claimed in claim 1, wherein the excitation optical system includes the second light being being directable by a second excitation optical system to the sample carrier in order to illuminate the entire surface of the latter.

12. The device as claimed in claim 11, wherein the second excitation optical system has a second deflecting mirror that directs the second light beam to the sample carrier.

13. The device as claimed in claim 11, wherein a first filter is provided between the sample carrier and the receiver in the beam path of the first fluorescent light, the first filter passing only the first fluorescent light.

14. The device as claimed in claim 1, wherein a first filter is provided between the sample carrier and the receiver in the beam path of the first fluorescent light, the first filter passing only the first fluorescent light.

15. The device as claimed in claim 14, wherein the first filter is a steep-edge filter.

16. The device as claimed in claim 1, wherein a second filter is provided in the beam path of the second fluorescent light between the sample carrier and the receiver, the second filter passing only the second fluorescent light.

17. The device as claimed in claim 16, wherein the second filter is a steep-edge filter.

18. The device as claimed in claim 1, wherein the receiver is a CCD arrangement including optical sensor elements that are arranged in accordance with a specific arrangement of the samples of the sample carrier.

* * * * *